Figure 1:
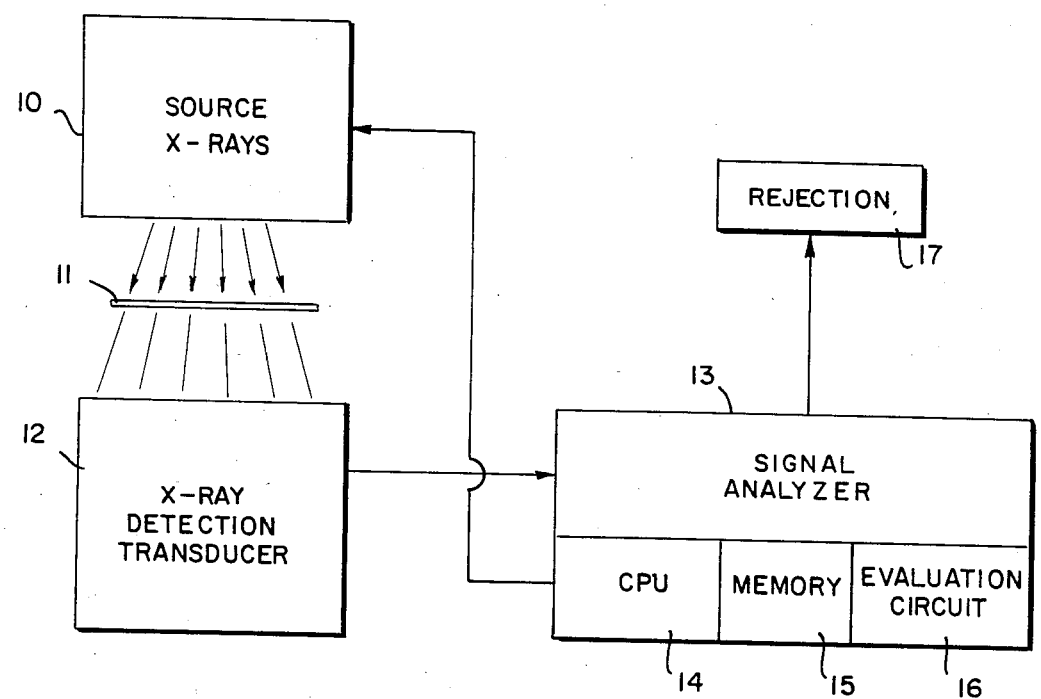

United States Patent [19]

Shideler et al.

[11] Patent Number: 4,549,306
[45] Date of Patent: Oct. 22, 1985

[54] SHEET METAL EVALUATOR

[75] Inventors: Anthony Shideler, Albany, Ind.; Dwight B. Raddatz, Woodridge, Ill.

[73] Assignee: Ball Corporation, Muncie, Ind.

[21] Appl. No.: 718,821

[22] Filed: Apr. 1, 1985

Related U.S. Application Data

[63] Continuation of Ser. No. 410,423, Aug. 23, 1982, abandoned.

[51] Int. Cl.[4] .............................................. G01T 1/16
[52] U.S. Cl. ......................................... 378/58; 378/56
[58] Field of Search ....................... 378/58, 57, 54, 55, 378/56

[56] References Cited

U.S. PATENT DOCUMENTS

| | | | |
|---|---|---|---|
| 2,632,117 | 3/1953 | Vossberg | 378/54 |
| 3,727,054 | 4/1973 | Herrick | 378/58 |
| 4,064,440 | 12/1977 | Roder | 378/57 |
| 4,415,980 | 11/1983 | Buchanan | 378/58 |

Primary Examiner—Craig E. Church
Attorney, Agent, or Firm—Gilbert E. Alberding

[57] ABSTRACT

An apparatus and method are disclosed for detecting voids in metal strip that are otherwise invisible through the use of X-ray radiation. The apparatus and method provide continuous and automatic inspection of sheet metal for localized voids through the continuous analysis of an electrical signal for departures from a norm, corresponding to homogeneousness, that represents such voids.

8 Claims, 3 Drawing Figures

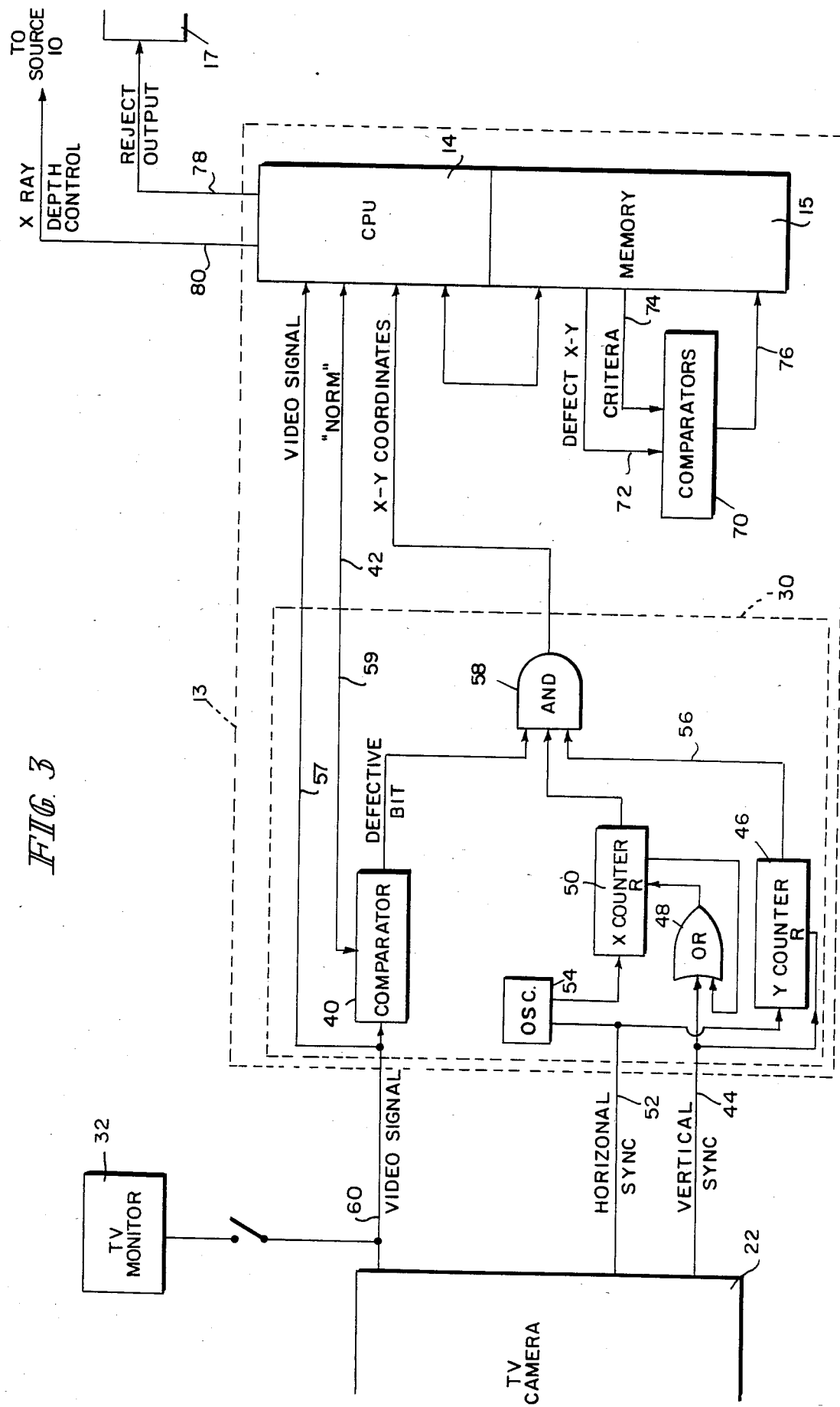

SHEET METAL EVALUATOR

This application is a continuation of application Ser. No. 410,423, filed Aug. 23, 1982 now abandoned.

This invention relates to an apparatus and method for determining imperfections in sheet metal, and particularly to an apparatus and method for automatically detecting invisible voids in metal strip from which can bodies are to be manufactured.

Metal strip, when rolled into a thin plate or strip, tends to have voids which, when the metal is formed, can fail under stress. Metal strip is exposed to extreme strain in the formation of metal can bodies by the draw-redraw and the draw and iron manufacturing methods. Discontinuities in the metal strip associated with voids frequently result in metal failure while the strip is in the metal-forming dies, causing equipment jam-ups that interfere with production, or inferior can bodies.

This invention provides a means and method for detecting such voids in metal strip that are otherwise invisible through the use of X-ray radiation. Although the use of X-rays to inspect articles of manufacture for interior flaws is known, the method and apparatus of this invention provides continuous and automatic inspection of sheet metal for localized voids through the continuous analysis of an electrical signal for departures from a norm, corresponding to homogeneousness, that represents such voids.

Such an invention includes a source of X-rays with sufficient energy to penetrate the metal strip, an X-ray detector capable of producing an electrical signal corresponding to the intensity of the penetrating X-rays, and an electrical signal analyzer for determining the presence of electrical signals corresponding to imperfections in the metal strip. Preferably, the signal analyzer includes a central processing unit, an associated memory and an evaluation circuit to compare the electrical signal with criteria stored in the memory that corresponds to voids in the metal strip.

By exposing the sheet metal to a source of penetrating X-rays, it is possible to convert the X-rays that penetrate the sheet metal into an electrical signal corresponding to the intensity of the penetrating X-rays. Where the sheet metal has voids, the intensity of the X-rays will be greater and the electrical signal will provide means to detect the voids. By analyzing the electrical signal for departures from the norm corresponding to homogeneity, an output may be provided which will signal the presence of defective sheet metal, or by means known in the art, mark or reject the defective sheet metal.

An X-ray detector capable of scanning an output produced by the penetrating X-rays may be used. Such a detector can produce an electrical signal corresponding to the X-ray penetration at localized areas of the metal sheet. Such an electrical signal can be analyzed by converting the signal from its analog character to a digital signal which represents the energy of the X-rays at localized points of the metal sheet. The digital signal can be compared with signal criteria stored in a memory by a control processing unit to detect localized voids in the sheet metal.

To improve the reliability of such inspection, the electrical signal may be analyzed and used to control the energy of the X-rays generated by the source of X-rays to thereby provide a signal norm that is consistent with variations in average metal thickness and composition.

For safety, the inspection apparatus and method should be performed in an enclosure that precludes the escape of X-ray radiation.

Further features and advantages of this invention may be apparent from the following drawings and further description.

Figure 2:
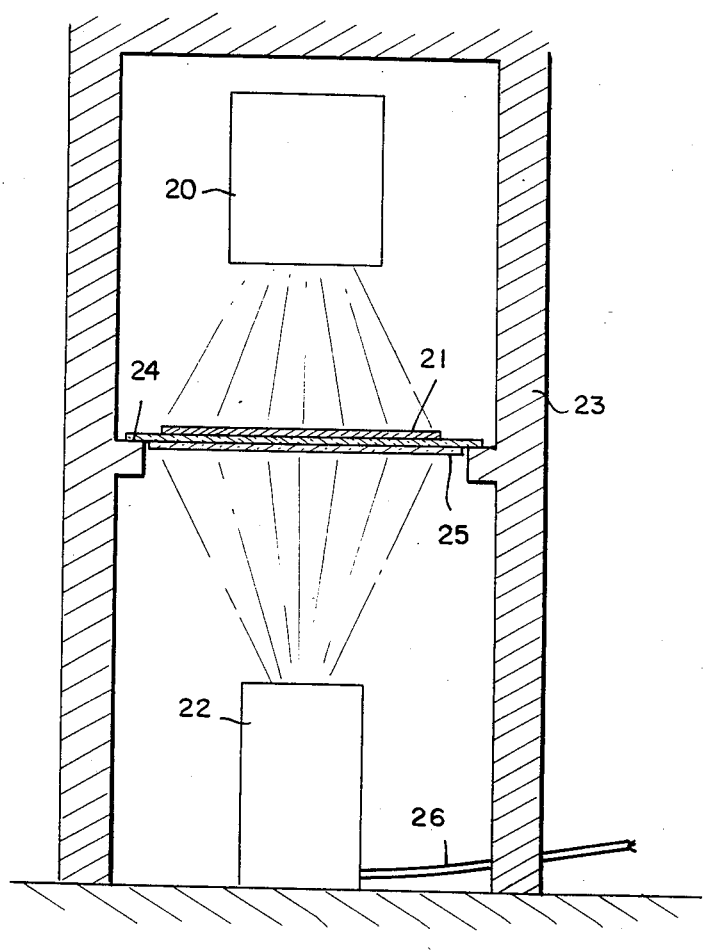

FIG. 1 is a basic block diagram of the invention;
FIG. 2 is a diagrammatic illustration of an arrangement of apparatus of this invention; and
FIG. 3 is a diagram of a signal evaluation circuit.

As shown in FIG. 1, a source of X-rays 10 is arranged to irradiate a metal sheet or metal strip 11. The X-rays that penetrate the metal strip 11 fall on an X-ray detection transducer 12. The X-ray detection transducer 12 produces an electrical signal that is dependent upon the intensity of the X-rays from source 10 that penetrate the metal sheet 11 and is indicative of departures from homogeneity in the metal sheet 11.

The electrical signal from the X-ray detection transducer is presented to a signal analyzer 13. The signal analyzer includes a central processing unit or CPU 14, memory 15, and an evaluator circuit 16 to determine the presence of electrical signals corresponding to imperfections in the metal sheet.

When an imperfection in the sheet metal is detected, the signal analyzer provides an output signal capable of energizing a rejection signal 17.

FIG 2 shows an arrangement of apparatus of this invention. The source of X-rays 20, metal strip 21, and X-ray detection transducer 22 are all enclosed in an enclosure 23 that precludes the escape of X-ray radiation from the enclosure and the entry of light radiation into the enclosure.

In this embodiment, the metal strip or metal sheet 21 rests upon a support 24 of rigid polymeric material, such as nylon or polypropylene. Because of its thickness and material content, support 24 does not absorb any significant energy from the X-rays. Where the metal strip is in coil form, its weight may be largely carried by the coil-conveying equipment and the support 24 may be used only to protect the X-ray sensitive detection system below it.

Below the metal strip in this embodiment is a florescent material 25 sensitive to X-ray radiation. The florescent material 25 will emit light radiation depending upon the intensity of the X-rays penetrating the metal sheet. If the metal sheet includes a localized void, X-rays of greater intensity will fall on the florescent material 25 adjacent the localized void, and the florescent material will produce more light energy corresponding to the sheet metal void.

In this embodiment, a TV camera is used as the X-ray detection transducer 22. An image orthicon is generally used in camera to detect variations in the emission level due to imperfections in the sheet metal. A variety of image orthicons are available for use and can provide usable signal levels at florescent illumination levels from less than 0.0005 foot candles to over 0.5 foot candles.

The optical system of the TV camera 22 is focused on the florescent material 25. The image of the emission of the florescent material is scanned by an electron beam of the image orthicon within the TV camera. The camera develops and amplifies an electrical signal that represents the level of florescent material emission (and thus the homogeneity of the sheet metal) from point to point over its surface. Where voids are present in the sheet metal, the increased localized emission of the florescent material will be detected in the TV camera and represented by increased signal levels at corresponding portions of the corresponding scans of the image of the florescent material. The TV camera thus generates a video signal that carries information on the homogeneity or imperfections present in the sheet metal.

The video signal may be conducted by an electrical cable 26 to the signal analyzer 13. One embodiment of a signal analyzer 13 for the video signal is illustrated in FIG. 3.

The video signal from the TV camera is coupled directly to a video digitizer 30 and may be coupled, by means of a selector switch 31, to a video monitor 32. The horizontal sweep and vertical sweep signals generated in the TV camera 22 are also coupled to the video digitizer 30 as separate signals.

The local video digitizer 30 converts the composite analog video signal from the TV camera to a digital signal that may represent a sheet metal defect and to digital X-Y coordinates that may be coupled to the CPU14. The X-Y coordinate signals and a "defective" bit are each stored in the memory 15 for use in determining if the sheet metal should be rejected. CPU 14 may be of any type conventionally known in the art, such as, for example, a PDP 1103 manufactured by Digital Equipment Corporation.

The CPU14 continuously computes an average signal value or "norm" corresponding to the homogeneity of the sheet metal. At each X and Y coordinate where the electrical signal level is significantly greater than the norm, the computer stores a "defective" bit and its X and Y coordinate in its associated memory 15. At the end of each scan of the florescent material 25, the "defective" bits and their X-Y locations are retrieved from the memory 15 and compared by CPU14 with criteria stored in memory 15 that corresponds to defective sheet metal. Such criteria may include one "defective" bit, or a specified number of "defective" bits at X-Y locations within a specified number of adjacent X-Y coordinates (for example, corresponding to a void).

Both the criteria corresponding to sheet metal imperfections and the programs for determination of average signal level and the X-Y location of each portion of the signal may be stored in the memory. The X-Y locations can be determined from the retrace signals generated by the TV camera at the end of each scan.

The Y location can be determined by counting the horizontal scan retrace signals. The TV camera generates 525 horizontal scans in two sweeps, or fields, of the image; 490 of the scans carry information from the image. The two fields are interlaced with one beginning at a point displaced one-half the length of the one line and generally about 1/250 of the image height above the others. At the end of each field, the TV camera generates vertical retrace and blanking signals which can be used to signal the beginning of each field and the count for determination of the Y coordinates of the signal.

The X coordinates also can be determined from the retrace and blanking signals. An oscillator can be provided to generate pulses for the X coordinates, with the X coordinate of each line after the beginning of each field to be determined by counting pulses after each horizontal retrace signal. On odd frames, the first line begins in the center of the image and only the last half of the oscillator pulses define the X coordinates of that line.

The video signal level representative of a "defective" bit can be determined by a voltage comparator circuit that compares the signal level with the norm and generates a "defective" bit if the signal level is greater than the signal norm.

During operation, the digitizer 30 compares the video signal level from the TV camera 22 with the video signal norm which is generated by CPU14. If the video signal generates a "defective" bit, the X-Y coordinates of the defective bit are stored in the memory 15. This sequence is repeated until the video levels of all parts of the metal sheet being inspected have been compared against the stored norm. A simplified weighting algorithm is used in the comparison process to allow for small variations in the video levels dependent upon the variations in conditions.

Upon the completion of each field, the stored X-Y coordinates of the defective bits are compared with stored criteria to determine the presence of metal imperfections. Utilizing a majority test rule, if the majority of X-Y values compare with the criteria, the operator is signalled by rejection signal 17 or the machine rejects or marks the defective sheet. The routines for the weighting and majority test algorithms are easily prepared using ordinary programming techniques and accordingly are not described herein in detail. However, other tests can be applied other than to majority test rule to determine whether the metal sheet is defective.

Refer now to FIG. 3 which includes a schematic illustration of the video digitizer 30. As mentioned above, the function of the video digitizer 30 is to convert the video signal level to a defective bit if it exceeds the signal norm at each X-Y coordinate and to generate a digital signal corresponding to the X-Y coordinate of the defective bit. In order to accomplish this, CPU14 sends the digital signal norm to comparator 40 over line 42. The vertical retrace signal from the TV camera 22 is coupled on line 44 to the Y counter 56 and to the OR gate 48. This vertical retrace signal is utilized to reset Y counter 46 and the X counter 50. At the same time, the horizontal sweep signal on line 52 triggers an oscillator 54 which increments the X counter 50. The oscillator can divide each line by any convenient number of pulses, for example, 256 counts for each horizontal sweep, i.e., each horizontal scan is divided into 256 X coordinate increments. The number 256 is arbitrarily selected here for the number of X axis increments since for each vertical sync interval there are 256 horizontal sweeps. The vertical axis is divided into 256 increments, the same as the X axis. The image is resolved into 65,536 elements (256×256).

At the end of each horizontal scan, i.e., after a count of 256, counter 50 generates a reset pulse which is coupled via OR gate 48 to the reset input of counter 50 to reset the counter. At the same time, the Y counter 46 is incremented one count by the horizontal retrace signal. Thus, in effect, counter 50 and counter 46 represent, respectively, the X coordinate and the Y coordinate of the instantaneous video signal on line 60. The digital signal corresponding to the X-Y coordinates of the video signal is coupled to AND gate 58 over line 56. The video signal is coupled to CPU14 over line 57 and to comparator 40 over line 60. Comparator 40 compares the video signal on line 60 with the digital signal norm on line 59. When a comparison exists in comparator 40, it develops a "defective" bit, and AND gate 60 is enabled and provides the X-Y coordinates of the defective bit to be stored in the memory 15 as directed by CPU14.

In addition to the determination of a signal "norm" from the video signal, CPU14 can provide a signal over line 80 to permit control of the energy of the X-rays generated by source 10, for example, to accommodate variations in sheet metal thickness.

Each of the respective X and Y coordinates of defective bits are thus coupled to a random access memory unit 15 of conventional design known in the art. These signals are stored in predetermined locations in the memory 15. At the end of each field, the X-Y coordinates of the stored defective bits from that image field are read out of memory 15 to the digital comparators 70 over line 72 in accordance with signals coupled thereto by the CPU14. At the same time, CPU14 reads out of memory 15 the criteria-information corresponding to a defect in the sheet metal to the digital comparators 70 over line 74 and stores the results of the comparison back in the memory 15 over line 76. Upon completion of the comparison for each field, the CPU14 analyzes the date in the memory 15 that resulted from the comparison in accordance with a stored program and makes a decision as to the presence or absence of a sheet metal defect. This decision triggers an output over line 78 to operate signal 17 or to operate machinery removing the defective material from the line or marking the defect.

While the present invention has been disclosed in connection with a preferred embodiment thereof, it should be understood that there may be other modifications of the present invention which fall within the spirit and scope of the appended claims.

What is claimed is:

1. A method of inspecting a metal sheet for invisible imperfections, comprising:
    exposing the metal sheet to X-rays having sufficient energy to penetrate the metal sheet;
    providing an image proportional to the intensity of X-rays that penetrate said metal sheet;
    scanning said image and converting said image into a first electrical signal which varies from point to point during the scan depending upon the intensity of the X-rays that penetrate said metal sheet at each point on said sheet;
    comparing said first electrical signal with a second electrical signal representing a norm for identifying defective bits for points on said sheet wherein said corresponding first electrical signal departs from said norm;
    generating signals corresponding to the X-Y coordinates or said sheet of said defective bits;
    comparing said defective bits corresponding to the X-Y coordinates of said sheets with stored criteria; and
    providing an output when the departure of said defective bits from said norm has characteristics similar to a metal imperfection.

2. The method of claim 1, wherein said scanning step includes scanning said image output in two dimensions.

3. Apparatus for detecting imperfections in sheet metal, comprising:
    a source of X-rays with sufficient energy to penetrate sheet metal;
    means for positioning sheet metal to be inspected before the source of X-rays;
    means for detecting the X-rays penetrating said sheet metal, said detecting means including means for determining the intensity of said X-rays penetrating said sheet metal over an area of said sheet metal, and for producing a first electrical signal corresponding to the intensity of said X-rays penetrating said sheet metal from point to point over said area of said sheet metal; and
    means for analyzing said first electrical signal for determining the presence of electrical signals corresponding to imperfections in said sheet metal, said analyzing means comprising:
    means for comparing said first electrical signal with a second electrical signal representing a norm for identifying defective bits of said first electrical signal corresponding to points over said area of said sheet metal wherein said first electrical signal departs from said norm and for generating digital signals corresponding to the representing said defective bits for each of said points; and
    means for comparing the digital signals for each of said points with criteria stored in a memory for determining the presence of imperfections in said sheet metal.

4. The apparatus of claim 3 wherein the means for analyzing the electrical signal includes a central processing unit, a memory, and an evaluation circuit.

5. Apparatus as recited in claim 3 and further including means for controlling the energy of the X-rays generated by said source as a function of the thickness of said metal sheet to provide a consistent norm.

6. Apparatus as recited in claim 3, wherein said detecting means includes means for emitting light radiation proportional to the intensity of the X-rays penetrating said sheet metal over said area of said sheet metal, and camera means for scanning an image of said emitted light radiation and for producing said first electrical signal.

7. Apparatus as recited in claim 6, wherein said light radiation-emitting means comprises a fluorescent material.

8. Apparatus for detecting imperfections in sheet metal, comprising:
    a controlled source of X-rays;
    means for positioning a metal sheet to be inspected before said source of X-rays;
    means for providing an image proportional to the intensity of X-rays that penetrate said metal sheet;
    an X-ray detector for scanning said image and for producing an electrical signal at each point of its scan that is proportional to the intensity of the penetrating X-rays;
    enclosure means for precluding radiation from entering or leaving the site of the X-ray source, the metal sheet, and the X-ray detector; and
    an electrical signal processing means including an analog-to-digital converter for said electrical signal, a central processing unit, an associated memory and an evaluation circuit for analyzing said electrical signal to provide an output to control the energy of the X-rays from said source to provide a consistent norm for said electrical signal, for analyzing departures of said electrical signal at each point of the scan from said norm, and for comparing defective bits of said electrical signal which depart from said norm with signal criteria for each point stored in said memory for determining the presence of imperfections in said sheet metal.

* * * * *